United States Patent [19]

Swindell

[11] Patent Number: 4,582,832
[45] Date of Patent: Apr. 15, 1986

[54] TRIMAZOSIN AS AN ANTI-ATHEROSCLEROSIS AGENT

[75] Inventor: Archie C. Swindell, Groton, Conn.

[73] Assignee: Pfizer Inc., New York, N.Y.

[21] Appl. No.: 770,128

[22] Filed: Aug. 28, 1985

Related U.S. Application Data

[63] Continuation-in-part of Ser. No. 658,845, Oct. 9, 1984, abandoned, which is a continuation of Ser. No. 471,965, Mar. 3, 1983, abandoned.

[51] Int. Cl.$^4$ .................. A61K 31/50; A61K 31/495; A61K 31/505
[52] U.S. Cl. ..................................... 514/254; 514/260
[58] Field of Search ............................... 514/254, 260

[56] References Cited

U.S. PATENT DOCUMENTS

| 3,669,968 | 6/1972 | Hess | 260/256.5 R |
| 4,130,647 | 12/1978 | Taylor | 424/251 |
| 4,150,119 | 4/1979 | Lalinde | 424/144 |
| 4,245,097 | 1/1981 | Shepherd | 546/245 |

Primary Examiner—Leonard Schenkman
Assistant Examiner—Joseph A. Lipovsky
Attorney, Agent, or Firm—Charles J. Knuth; Albert E. Frost; Peter C. Richardson

[57] ABSTRACT

The use of trimazosin or a pharmaceutically acceptable acid addition salt thereof as an agent for retarding the development of atherosclerosis in a mammal, especially for retarding and reducing the development of fibrous plaques associated with atherosclerosis.

4 Claims, No Drawings

TRIMAZOSIN AS AN ANTI-ATHEROSCLEROSIS AGENT

CROSS REFERENCE TO RELATED APPLICATION

This application is a continuation-in-part of application Ser. No. 658,845, filed Oct. 9, 1984, now abandoned, which, in turn is a continuation of application Ser. No. 471,965, filed Mar. 3, 1983, now abandoned.

BACKGROUND OF THE INVENTION

1. Field of the Invention

This invention relates to the use of trimazosin or a pharmaceutically acceptable acid addition salt thereof for retarding the development of arterial disease in mammals. More specifically it relates to a method for suppressing fibrosis of atherosclerotic plaques in mammals having atherosclerosis by administering to said mammals trimazosin or a pharmaceutically acceptable acid addition salt thereof.

2. Description of the Prior Art

Atherosclerosis, a disease of the arteries, is recognized to be the leading cause of death in the United States and Western Europe. The pathological sequence leading to atherosclerosis and occlusive heart disease has been described in detail by Ross and Glomset in New England Journal of Medicine 295, 369–377 (1976). The earliest stage in this sequence is the formation of "fatty streaks" (plaques) in the carotid, coronary and cerebral arteries and in the aorta. These in turn give rise to development of the "fibrous plaque", which consists of accumulated intimal smooth muscle cells laden with lipid and surrounded by extracellular lipid, collagen, elastin, and proteoglycans. The cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the "complicated lesion" which accounts for the arterial occlusion and tendency toward mural thrombosis and arterial muscular spasm that characterize advanced atherosclerosis.

Statistical evidence suggests that hyperlipidemia, and hypertension are primary risk factors in causing atherosclerosis. Treatment of atherosclerosis is, therefore, approached by attempts to control hypertension and hyperlipidemia, by dietary or pharmacological means. Some success has been achieved in reducing the incidence and severity of atherosclerosis by strict adherence to a prudent diet, by lowering plasma lipids with drugs or with ileal bypass surgery, and by lowering systemic blood pressure with diet or drugs. However, coronary heart disease remains a threat, even to individuals striving to control their risk factor levels. It has been speculated that every individual in the United States has some degree of atherosclerosis. This fact, along with the high associated mortality and the inadequacy of present treatment methods, establishes the need for an anti-atherosclerotic agent.

The use of trimazosin and its pharmaceutically acceptable acid addition salts as antihypertensive agents is described in U.S. Pat. No. 3,669,968; and their use for the treatment of congestive heart failure and ischemic heart disease is disclosed in U.S. Pat. No. 4,130,647.

However, in spite of the above-mentioned uses for trimazosin and its salts, there was, prior to the time of the present invention, no report of the intent to use trimazosin or its salts for retarding the development of atherosclerosis, and no appreciation of its role, or that of its pharmaceutically acceptable acid addition salts, in achieving said desirable goal.

SUMMARY OF THE INVENTION

It has now been found that trimazosin or a pharmaceutically acceptable acid addition salt thereof when administered to a mammal having an atherosclerotic condition produces a direct therapeutic benefit in retarding the further development of atherosclerosis in said mammal. More specifically, trimazosin, or one of its said salts, when administered in an atherosclerotic treating amount to a mammal having atherosclerosis, suppresses formation of fibrotic lesions or plaque.

The high incidence of atherosclerosis in the United States noted above, gives rise to normotensive individuals free of congestive heart disease and/or ischemic heart disease, problems normally considered as cardiac complications of hypertension.

The direct therapeutic benefit of trimazosin and its above-mentioned acid addition salts in retarding the development of arterial disease in such individuals appears to be independent of changes in blood pressure or in serum lipid levels, and occurs at clinically relevant levels of drug.

DETAILED DESCRIPTION OF THE INVENTION

Trimazosin, known chemically as 2-hydroxy-2-methylpropyl-4-(4-amino-6,7,8-trimethoxy-2-quinazolinyl)-1-piperazine carboxylate, and its pharmaceutically acceptable acid addition salts, are described in U.S. Pat. No. 3,669,968; issued June 13, 1972.

Although the generic name of trimazosin represents the free base, the present invention is also meant to embrace its pharmaceutically acceptable acid addition salts, such as hydrochloride, hydrobromide, hydroiodide, nitrate, sulfate, bisulfate, phosphate, acid phosphate, acetate, lactate, citrate, acid citrate, tartrate, bitartrate, succinate, maleate, gluconate, methanesulfate, ethanesulfate, benzenesulfonate and p-toluenesulfonate salts.

In the treatment of atherosclerosis, trimazosin can be administered via the oral or parenteral routes. However, it is generally preferred to administer trimazosin or its pharmaceutically acceptable acid addition salts orally. In general, these compounds are most desirably administered in doses ranging from about 10 mg up to about 600 mg per day, although variations will still necessarily occur depending upon the weight of the subject being treated. However, a dosage level that is in the range of from about 0.16 mg to about 9.6 mg per kg of body weight per day is most desirably employed in order to achieve effective results, with a preferred oral range in man being about 2.5–5.0 mg/kg. Nevertheless, it is still to be appreciated that other variations may also occur in this respect, depending upon the species of animal being treated and its individual response to said medicament, as well as on the particular type of pharmaceutical formulation chosen and the time period and interval at which such administration is carried out. In some instances, dosage levels below the lower limit of the aforesaid range may be more than adequate, while in other cases still larger doses may be employed without causing any harmful or deleterious side effects to occur provided that such higher dose levels are first divided into several smaller doses that are to be administered throughout the day.

For purposes of oral administration, tablets containing various excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in soft elastic and hard-filled gelatin capsules; preferred materials in this connection also include lactose or milk sugar as well as high molecular weight polyethylene glycols. When aqueous suspensions and/or elixirs are desired for oral administration, the essential active ingredient may be combined with various sweetening or flavoring agents, coloring matter or dyes and, if so desired, emulsifying and/or suspending agents, together with such diluents as water, ethanol, propylene glycol, glycerin and various like combinations thereof.

Although the preferred mode of administration of trimazosin or one of its pharmaceutically acceptable acid addition salts is oral, they may be administered parenterally as well.

For purposes of parenteral administration, solutions of these particular compounds in sesame or peanut oil or in aqueous propylene glycol may be employed, as well as sterile aqueous solutions of the corresponding water-soluble acid addition salts previously enumerated. Such aqueous solutions should be suitably buffered if necessary and the liquid diluent rendered isotonic with sufficient saline or glucose. These particular aqueous solutions are especially suitable for intravenous, intramuscular and subcutaneous injection purposes. In this connection, the sterile aqueous media employed are readily obtained by standard techniques well known to those skilled in the art. For instance, distilled water is ordinarily used as the liquid diluent and the final preparation is passed through a suitable bacterial filter, such as a sintered-glass filter, or a diatomaceous-earth or unglazed porcelain filter. Preferred filters of this type include the Berkefeld, the Chamberland and the asbestos disc-metal Seitz filter, wherein the fluid is sucked through the filter candle into a sterile container with the aid of a suction pump. Needless to say, the necessary steps should be taken throughout the preparation of these injectable solutions to ensure that the final products are obtained in a sterile condition.

Various procedures and diets have been tested in the rabbit and other animal species in an effort to identify a convenient and accurate model for human atherosclerosis. Initially, diets with added cholesterol were fed to rabbits, and fatty infiltration of their aortas and other arteries were noted. These lesions were composed of lipid filled "foam" cells. They are now known to resemble, both morphologically and biochemically, the benign fatty streak found in human arteries, rather than the raised fibrous plaque (Wissler et al., in G.R.V., Factors in Formation and Regression of the Atherosclerotic Plaque, Plenum Press, New York, pp. 59–78, 1982). In 1971, Kritchevsky and coworkers added various edible oils to a high-cholesterol diet in rabbits, and reported that the diet containing 8% peanut oil plus 2% cholesterol caused aortic lesions which were more severe and of markedly elevated collagen content relative to those caused by cholesterol alone or with other oils (Kritchevsky et al., Atherosclerosis 14; 53–64, 1971). This model of fibrous-fatty aortic atherosclerosis has since been used by many investigators, as recently summarized by Camejo (Advances in Lipid Research 19, 1–53, 1982), and was used in the study of trimazosin described here. Extrapolation to, and correlation of this procedure, with human utility is accepted by investigators in this field.

The study comprised 60 male New Zealand White rabbits, body weight 2 to 3 kg, randomly divided into 6 groups, 10 animals per group. It followed the procedure of Kramsch et al., J. Clin. Invest. 65, 967–981 (1980). The study lasted 12 weeks, during which time animals in each group received diets plus drug as follows. Normal control (NC) rabbits were fed standard pelleted laboratory rabbit chow. The N80 group was fed standard rabbit chow mixed with sufficient trimazosin to supply a dose of 80 mg/kg/day of the hydrochloride salt. Atherogenic controls (AC) received a fibrogenic-atherogenic diet consisting of rabbit chow pellets thoroughly mixed with peanut oil (8%) and cholesterol (2%) (Kritchevsky et al. loc cit.). Groups A20, A30 and A80 were fed the fibrogenic-atherogenic diet mixed with amounts of trimazosin hydrochloride to supply doses of 20, 30 and 80 mg/kg/day of trimazosin hydrochloride, respectively.

Blood pressures were measured by the tail-cuff method (Kramsch et al., Abstr. 29th Annual Session, Am. Assoc. of Lab. Animal Science, Abstr. No. 38, 1978) for animals in the A80, A30, A20, AC and NC groups, prior to the study or during week 4 or 8 of the study. Measurements during the study were made 4 hours after offering the daily 100 g ration (which also contained the daily drug dose, for animals receiving drug). Blood levels of trimazosin were also measured in several of the A80 animals under similar circumstances, and were found to be 10–40 micrograms/ml, depending on the amount of medicated diet individual animals had consumed.

Measured under these conditions, blood pressures in all the rabbits were within the normal range throughout the study. The fibrogenic-atherogenic diet did not induce hypertension. No change was associated with administration of trimazosin at week 8 of the study. The rabbits clearly did not experience chronic hypotension during the study, indicating that changes in aortic composition found subsequently were not mediated by a hypotensive response to trimazosin.

Serum cholesterol levels were measured in all rabbits periodically throughout the study, and were found at 8–12 weeks to be in excess of 2000 mg/dl in all rabbits being fed the fibrogenic-atherogenic diet. Trimazosin had no effect on cholesterol levels, so that aortic changes associated with its administration were unlikely to be mediated through diminished hyperlipidemia.

After 12 weeks on study, the rabbits were sacrificed and autopsied, and standardized segments of aortas were excised. The degree of involvement of the aortic surface was determined by staining and quantitative planimetry. Small areas of plaques were fixed for histopathology. The intima plus media were stripped from the aortas, and were analyzed for dry weight and dry delipidated weight, and for content of the following constituents: cholesterol, cholesterol ester, collagen, elastin, calcium, and phosphorus.

The aortas of the AC rabbits fed fibrogenic-atherogenic diet without trimazosin, showed statistically significant increases in intimal-medial content of the above constituents compared to chow-fed controls. Collagen was increased by 46%, elastin was increased by 27%, delipidated dry weight was increased by 32%, and phosphorus was increased by 460%. In the fat-fed groups, trimazosin caused a dose-responsive decrease in all four of these aortic constituents, to levels not significantly different from those of the chow-fed controls. There were no detectable differences in any parameter measured between the N80 and the NC groups.

Histological sections were prepared from areas of aortic plaques from control and treated fat-fed animals. Plaques from aortas of A80 animals were filled with foam cells, lacked significant amounts of observable collagen, and closely resembled foam-cell lesions seen in rabbits fed cholesterol without peanut oil, from other studies. Significant amounts of collagen were present in sections from the present atherogenic control animals.

From dose-response curves, the optimal dose for all effects of trimazosin on aortic composition was 30-40 mg/kg/day. Blood levels of trimazosin were measured in several of these same animals between two and six hours after beginning consumption of their daily medicated ration. Trimazosin concentrations at the 30-40 mg/kg dose level were in the range of 15-25 micrograms/ml, similar to clinically effective levels observed in man during the treatment of hypertension.

In the AC rabbits fed fibrogenic atherogenic diet without trimazosin, an average of 17% of the area of the aorta was involved with atherosclerotic plaques, and there were large increases in aortic cholesterol, both free and esterified, compared to NC animals. Aortic calcium content was elevated, but levels were erratic, and effects were not statistically significant. In the A80 group, the degree of aortic involvement with plaque was decreased to 10%, but the effect was not statistically significant. Aortic cholesterol contents in all the trimazosin treatment groups fed the fibrogenic atherogenic diet were higher than the AC group, but the increases were not statistically significant.

Thus, administration of trimazosin to rabbits during development of fibrotic fatty aortic plaques caused these lesions to closely resemble the benign fatty streak rather than the raised fibrotic plaque of human atherosclerosis.

I claim:

1. A method of suppressing fibrosis of atherosclerotic lesions in a non-hypertensive mammal free of ischemic heart disease and of congestive heart failure but having atherosclerosis which comprises administering to said mammal a fibrosis lesion suppressing amount of trimazosin or a pharmaceutically acceptable acid addition salt thereof.

2. The method of claim 1 wherein trimazosin is administered.

3. The method of claim 2 wherein the trimazosin is administered orally.

4. The method of claim 3 wherein the trimazosin is administered orally at from about 0.16 mg/kg/day to about 9.6 mg/kg/day.

* * * * *